United States Patent
Lawrence

(10) Patent No.: US 10,830,726 B2
(45) Date of Patent: Nov. 10, 2020

(54) ELECTROCHEMICAL PH SENSOR COMPRISING A PHENOLIC COMPOUND USING HYDROGEN BONDING OF THE HYDROXYL GROUP TO SULPHUR ATOMS OF THE PHENOLIC COMPOUND

(71) Applicant: ANB Sensors Limited, Cambridge, Cambridgeshire (GB)

(72) Inventor: Nathan Lawrence, Cambridge (GB)

(73) Assignee: ANB SENSORS LIMITED, Cambridge (GB)

( * ) Notice: Subject to any disclaimer, the term of this patent is extended or adjusted under 35 U.S.C. 154(b) by 107 days.

(21) Appl. No.: 16/306,461

(22) PCT Filed: Jun. 1, 2017

(86) PCT No.: PCT/GB2017/051570
§ 371 (c)(1),
(2) Date: Nov. 30, 2018

(87) PCT Pub. No.: WO2017/208000
PCT Pub. Date: Dec. 7, 2017

(65) Prior Publication Data
US 2019/0178831 A1 Jun. 13, 2019

(30) Foreign Application Priority Data
Jun. 2, 2016 (GB) .................. 1609669.5

(51) Int. Cl.
*G01N 17/00* (2006.01)
*G01N 27/26* (2006.01)
*G01F 1/64* (2006.01)
*G01N 27/30* (2006.01)
*G01N 27/416* (2006.01)
*G01N 27/48* (2006.01)
*G01N 33/18* (2006.01)

(52) U.S. Cl.
CPC ....... *G01N 27/302* (2013.01); *G01N 27/4167* (2013.01); *G01N 27/48* (2013.01); *G01N 33/18* (2013.01)

(58) Field of Classification Search
CPC .................. G01N 27/302; G01N 27/4167
See application file for complete search history.

(56) References Cited

U.S. PATENT DOCUMENTS

| 5,223,117 A | 6/1993 | Wrighton et al. |
| 2012/0132544 A1* | 5/2012 | Lawrence .......... G01N 27/4167 205/782 |
| 2014/0332398 A1 | 11/2014 | Lawrence et al. |

OTHER PUBLICATIONS

Arai et al., "Preparation of carbon electrodes modified with poly(mercaptohydroquinone)s and their functions as pH sensor," Chemistry Letters, pp. 867-868, 1986 (Year: 1986).*

(Continued)

*Primary Examiner* — Angelo Trivisonno
(74) *Attorney, Agent, or Firm* — Kilpatrick Townsend & Stockton LLP

(57) ABSTRACT

An electrochemical pH sensor for measuring pH in a low buffer and/or low ionic strength analyte where the electrochemical pH sensor comprises an electrode coupled with a phenolic redox species and the chemistry of the redox species provides for hydrogen bonding to one or more sulphur atoms of the redox species.

14 Claims, 5 Drawing Sheets

(56) References Cited

OTHER PUBLICATIONS

International Search Report and Written Opinion for International Application No. PCT/GB2017/051570, dated Sep. 15, 2017. (11 pages).
Arai, et at., "Preparation of Carbon Electrodes Modified With Poly(Mercaptohydroquinone)s and Their Functions As pH Sensor", Chemistry Letters, Jun. 5, 1986, pp. 867-868, The Chemical Society of Japan. (2 pages).
Batchelor-McAuley, et al., "Voltammetric Responses of Surface-Bound and Solution-Phase Anthraquinone Moieties in the Presence of Unbuffered Aqueous Media", J. Phys. Chem. C, 2011, 115(3), pp. 714-718 (5 pages).

\* cited by examiner

ELECTROCHEMICAL PH SENSOR COMPRISING A PHENOLIC COMPOUND USING HYDROGEN BONDING OF THE HYDROXYL GROUP TO SULPHUR ATOMS OF THE PHENOLIC COMPOUND

CROSS-REFERENCE TO RELATED APPLICATIONS

This application is a U.S. National Stage of International Application No. PCT/GB2017/051570, filed Jun. 1, 2017, which claims the benefit of Great Britain Patent Application No. 1609669.5 filed on Jun. 2, 2016, the entire disclosures of which are hereby incorporated by reference in their entireties.

BACKGROUND

Embodiments of the present application provide for electrochemical pH sensing using an active redox species comprising a phenolic compound, wherein the phenolic compound includes a sulphurous atom attached either directly or indirectly to the aromatic ring of the phenolic compound and configured to form a hydrogen bond with the hydrogen atom associated with the hydroxyl moiety of the phenolic compound.

In chemistry, pH is a numeric scale used to specify the acidity or basicity (alkalinity) of an aqueous solution. It is approximately the negative of the logarithm to base 10 of the molar concentration, measured in units of moles per liter of hydrogen ions. More precisely, it is the negative of the logarithm to base 10 of the activity of the hydrogen ion. Solutions with a pH less than 7 are acidic and solutions with a pH greater than 7 are basic. Pure water is neutral, being neither an acid nor a base.

pH measurements are important in agronomy, medicine, biology, chemistry, agriculture, forestry, food science, environmental science, oceanography, civil engineering, chemical engineering, nutrition, water treatment and water purification, as well as many other industries/applications.

For nearly a century, pH has most commonly been measured using a glass electrode. The glass electrode is a combination electrode that combines both a glass and a reference electrode into one body. The combination electrode consists of the following parts: a sensing part of the electrode, a bulb made from a specific glass; an internal electrode, usually silver chloride electrode or calomel electrode; an internal solution, usually a pH=7 buffered solution of 0.1 mol/L KCl or $1 \times 10^{-7}$ mol/L HCl; a reference electrode, usually the same type with a reference internal solution, usually 0.1 mol/L KCl; a junction with studied solution, usually made from ceramics or capillary with quartz fiber; and the body of the electrode, made from non-conductive glass or plastics.

Glass electrodes cannot be used in many industries because of their fragility, requirement of calibration before use, and need to be stored under appropriate conditions, such as the requirements that the sensor be stored wet. As such, there has been a need for a new method of determining pH that overcomes these operational problems.

A number of chemical analysis tools are known from chemical laboratory practice. Such known analysis tools include, for example various types of chromatography, electrochemical and spectral analysis. Of the analysis tools, the potentiometric method has been widely used for the measurements of water composition both in the laboratory and in the field of ground water quality control.

U.S. Pat. No. 5,223,117 (Wrighton) discloses a two-terminal voltammetric microsensor having an internal reference using molecular self-assembling to form a system in which the reference electrode and the indicator electrode are both on the sensor electrode. The reference molecule is described as a redox system that is pH-insensitive, while the indicator molecule is pH sensitive and is formed by a hydroquinone based redox system having a potential that shifts with the pH. Both, reference molecule and indicator molecule layers are prepared by self-assembly on gold (Au) microelectrodes. In the known micro-sensor of Wrighton, a pH reading is derived from analysis of peak readings of the voltammograms, i.e., the shift of the peak reading obtained from the pH sensitive indicator molecule (often referred to as the redox active species).

Recently there has been significant work in the development of pH sensors for use in the water industry, where the concentration of dissolved buffer and/or ionic salt is low. Interest in this area stemmed from the work by Compton et al. (see C. Batchelor-McAuley, B. R. Kozub, D. Menshkau, R. G. Compton, *Voltammetric Responses of Surface-Bounda And Solution-Phase Anthraquinone Moieties in the Presence of Unbuffered Aqueous Media*, J. Phys. Chem. C 115, pp. 714-718 (2011)), who showed the use of classical quinone/hydroquinone voltammetry to monitor pH in these systems failed. Compton established that the proton coupled electrochemical process perturbed the pH of the solution locally to the electrode when little or no buffer and/or ionic salt was in the analyte solution.

To this end, work by Dr. Nathan Lawrence has shown that this issue can be mitigated by the use of a variety of quinone and phenol based systems, which provide a means of internal hydrogen bonding of the proton being transferred in the electrochemical process. In this work, it was shown that dihydroxyanthraquinone and alizarin were suitable for the quinone systems, where the keto moiety closest to the —OH moiety allowed the facilitation of the proton coupled electron transfer and providing a means for the reaction to follow a concerted rather than non-concerted mechanism. Further to these results, it was shown that oxidation of phenol species containing moieties holding keto groups in the 2-position of the benzene ring, e.g., salicyaldehyde, provided an electroactive polymer species that is pH active and able to measure pH in low buffered media/ionic strength, such as water/seawater. A variety of derivatives were tested by Lawrence and described in U.S. Patent Publication No. 2014/0332398, including the aldehyde, ester and nitrogen based compounds.

As well as measuring pH in water, there is also a need to measure pH in seawater, saline solutions and other low buffer/low ionic strength analytes. One important reason for measuring pH in saltwater is to monitor the effects of carbon dioxide in the atmosphere on the pH of the Oceans. As part of its operational definition of the pH scale, the IUPAC defines a series of buffer solutions across a range of pH values (often denoted with NBS or NIST designation). These solutions have a relatively low ionic strength (~0.1) compared to that of seawater (~0.7), and, as a consequence, are not recommended for use in characterizing the pH of seawater, since the ionic strength differences cause changes in electrode potential. To resolve this problem, an alternative series of buffers based on artificial seawater have been developed. This new series of buffers resolves the problem of ionic strength differences between samples and the buffers, and the new pH scale is referred to as the 'total scale', often denoted as pHT. The total scale was defined using a medium containing sulfate ions. These ions experience protonation, $H^+ + SO_4^{2-} \leftrightarrows HSO_4^-$, such that the total scale includes the effect of both protons (free hydrogen ions) and hydrogen sulfate ions: $[H^+]T=[H^+]F+[HSO_4^-]$.

In addition to water and seawater, the need for measuring pH in low buffer/low ionic strength analytes includes measuring pH in saline solutions and the like in medical processes, measuring pH in pharmaceutical testing of solutions that may often be low buffer/low ionic strength solutions, measuring pH in food and beverage processes and/or the like.

A problem associated with the previously described quinone and phenol based systems for low buffer operation, such as in water/seawater, is that the systems cannot be used for prolonged use in water/seawater monitoring because of instability and because the systems produce low accuracy/precision. These issues stem from the solubility of the described quinone systems in aqueous media, causing leaching from the electrode surface over time and the poor polymerisation in the described phenol system, which produces a poor voltammetric output (structural issues with the redox species may cause splitting of the potentiometric peak making accurate measurements using the potentiometric peak extremely difficult).

SUMMARY

Embodiments of the present disclosure provide an electrochemical sensor for detecting and monitoring pH of low buffer and/or low ionic strength analytes, such as water, seawater, saline solutions and/or the like. Embodiments of the present disclosure provide a pH sensor using a redox active chemistry comprising a phenolic compound, wherein the phenolic compound includes a sulphurous atom attached either directly or indirectly to the aromatic ring of the phenolic compound and configured to form a hydrogen bond with the hydrogen atom associated with the hydroxyl moiety of the phenolic compound.

In some embodiments, the phenol species contains a sulphur moiety, where the phenol species is configured to provide for the formation of hydrogen bonding through either a five (5) member and/or six (6) member ring containing a sulphur-hydrogen bonding.

In embodiments of the present disclosure, the sulphur moiety provides a molecular structure that can be formed into stable polymers that can be used for long term pH monitoring and can provide accurate/precise pH measurement.

In some embodiments of the present disclosure, the phenol species containing the sulphur-hydrogen bonding forms a stable polymer on the sensing electrode of an electrochemical pH sensor, where the polymer does not passivate the electrode and the polymer formed on the sensing electrode maintains a configuration for hydrogen bonding through the polymer facilitating pH measurement in low buffer/low ionic strength analytes.

The concentration of protons or its logarithm pH can be regarded as the most critical parameter in water chemistry. It determines the rate of many important chemical reactions as well as the solubility of chemical compounds in water. In some embodiments of the present disclosure, the redox species containing the sulphur-hydrogen bonding provides for pH measurement in low buffer/low ionic strength analytes, such as water, seawater, saline solutions, beverages, saline solutions and/or the like. Moreover, the polymers of the present application provide a stable chemistry that provides for pH monitoring over long periods of time and that is capable of measuring pH from at least the range of 3 to 12.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

Figure 1:
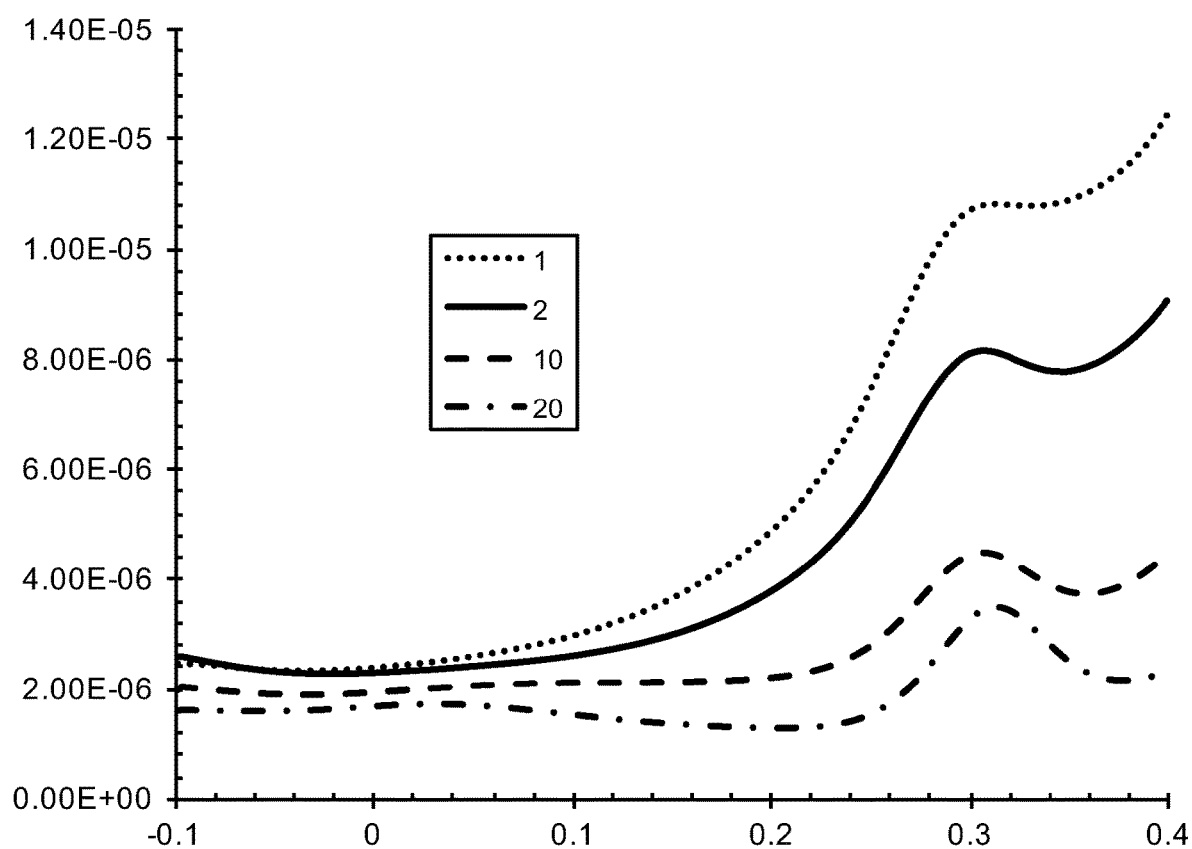
FIG. 1 illustrates voltammetric scans 1, 2, 10 and 20 from an electrode comprising a phenol derivative containing a sulphur moiety, in accordance with embodiments of the present disclosure, when placed in a pH 4 solution.

The ensuing description provides some embodiment(s) of the invention, and is not intended to limit the scope, applicability or configuration of the invention or inventions. Various changes may be made in the function and arrangement of elements without departing from the scope of the invention as set forth herein.

Some embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure and may start or end at any step or block. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium"

includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded or transmitted via any suitable means including memory sharing, message passing, token passing, network transmission, etc.

Reference will now be made in detail to embodiments, examples of which are illustrated in the accompanying drawings and figures. In the following detailed description, numerous specific details are set forth in order to provide a thorough understanding of the subject matter herein. However, it will be apparent to one of ordinary skill in the art that the subject matter may be practiced without these specific details. In other instances, well known methods, procedures, components, and systems have not been described in detail so as not to unnecessarily obscure features of the embodiments. In the following description, it should be understood that features of one embodiment may be used in combination with features from another embodiment where the features of the different embodiment are not incompatible.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step. The first object or step, and the second object or step, are both objects or steps, respectively, but they are not to be considered the same object or step.

The terminology used in the description of the disclosure herein is for the purpose of describing particular embodiments only and is not intended to be limiting of the subject matter. As used in this description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting", depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Embodiments of the present invention provide a new set of derivatives for the electrochemical determination of pH in low electrolyte/buffer media consistent with the conditions found in drinking water, source water, saline solution, pharmaceutical solutions and/or the like and/or high ionic strength media that are naturally buffered, but are unable to resist changes in local pH where proton transfer is unfacilitated. In the embodiments, the phenol group includes a sulphur moiety, which provides a redox chemistry that can produce a stable polymer on an electrode to provide for long duration operation and accurate/precise pH measurement.

In some embodiments of the present invention, phenol derivatives are based on the formation of hydrogen bonding through either a five (5) member and/or six (6) member ring containing sulphur-hydrogen bonding. The ability for sulphur to hydrogen bond through five or six membered rings provides far better flexibility of structure type than the oxygen and nitrogen moieties proposed to date. As such, structures described herein provide for improved pH measurement in water/seawater. Surprisingly, it has been found that the sulphur structures described herein provide greatly improved facilitation of proton transfer, improving pH sensing performance. Furthermore, in some embodiments of the present disclosure, the sulphur to hydrogen bond through five or six membered rings provides for a well-defined redox active polymeric species. This well-defined polymeric species provides for stability across the entire pH range, unlike previous structures that do not have stability and as a result cannot be used for accurate and/or long-term pH monitoring. In fact, previous structures were found to be unstable for long-term monitoring.

Merely by way of example, the following describe some of the structures of redox active polymeric species that may be used in pH sensors, in accordance with some embodiments of the present disclosure include:

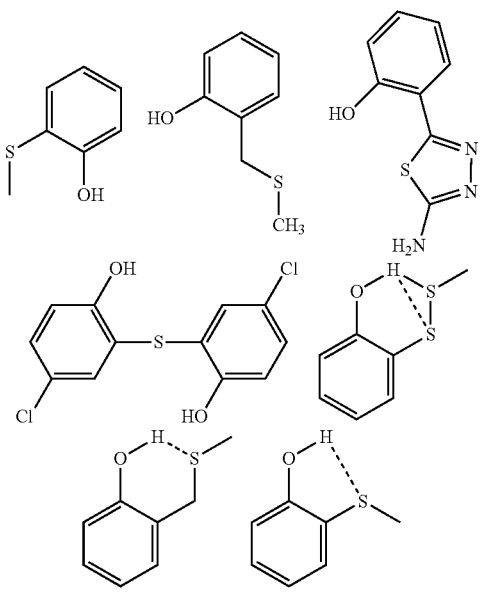

In some embodiments of the present disclosure, the electrochemical pH sensor comprises 2-(methylthio)phenol (see below).

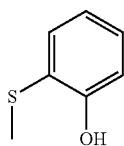

This embodiments of a pH sensor was used to make accurate measurement of pH in both source and salt water.

Embodiments of the present disclosure, were used in a pH sensor with off-the shelf chemicals used without further purification. The buffered solutions were made in accordance with the IUPAC standards.

Measurement from electrochemical measurements were recorded using an PGSTAT30 Autolab potentiostat (Ecochemie, Netherlands) with a standard three-electrode configuration. A platinum wire (1 mm diameter) provided the counter electrode and a calomel electrode acted as the reference. Glassy carbon (GC) acted as the working electrode. All square wave voltammetric experiments were conducted using the following parameters: Frequency=25 Hz, Step Potential=2 mV, Amplitude=20 mV.

Details of the synthetic seawater are outlined below:

| Parameter | Level | Range | Units |
|---|---|---|---|
| pH | 8.3 | 8.2-8.4 | |
| dkH | 10.5 | 10-11 | |
| Calcium | 440 | 430-460 | mg/l |
| Magnesium | 1340 | 1300-1380 | mg/l |
| Chloride | 19550 | 19960-20130 | mg/l |
| Potassium | 410 | 380-420 | mg/l |

Advantageously, the pH active redox active species were insoluble in aqueous media, therefore to study their electrochemical response they were solvent cast onto the electrode surface. However, in some embodiments of the present disclosure, the pH active/redox active species may be included in a carbon paste or a carbon epoxy, immobilized within an electrode using a carbon press, screen-printed onto an electrode and/or the like. In fact, the sulphur redox species described herein form versatile redox polymers that can be effectively applied to the sensing electrode of a pH sensor. For the solvent casting, a solution of the chemical was prepared in THF (1 mg/mL) and a 20 uL aliquot of this solution was pipette onto the electrode surface and allowed to dry in the air. Once dry the electrode was ready to use.

Embodiments of the present disclosure were used to derive data examining the voltammetric response of the 2-methylthiophenol in pH 4 aqueous media. The potential range was minimized to ensure that over oxidation of the phenol species and passivation of the electrode was inhibited. However, in the testing, it was found that unlike with other chemistries, the phenol species containing the sulphur moiety was resistant to over oxidation and did not passivate the electrode. This is a significant advantage of the new redox chemistry over existing solutions FIG. 1 details scans 1, 2, 10 and 20 of the modified electrode when placed in the pH 4 solution. Scan 1 shows a broad oxidation wave at +0.31 V with a shoulder at +0.31 V, due to the oxidation of the phenol species. The scans show the emergence of a now well-defined wave at +0.31 V and a decrease in the phenol oxidation wave, this is due to the formation of an electroactive polymeric species on the electrode surface. The chemical configurations in accordance with embodiments of the present disclosure form an electroactive polymeric species that does not, unlike previously described configurations, passivate the electrode.

Scans 10 and 20 show, due to the formation of the non-passivating electroactive polymeric species on the sensor electrode, the enhancement and resolution of this new oxidation wave and the subsequent loss of the parent phenol oxidation. The new oxidation wave can be attributed to the formation of a polymeric species on the electrode surface consistent with the oxidation of salicylic acid and its derivatives.

The polymer modified electrode, in accordance with some embodiments of the present disclosure, was next tested in a range of pH solutions.

Figure 2:
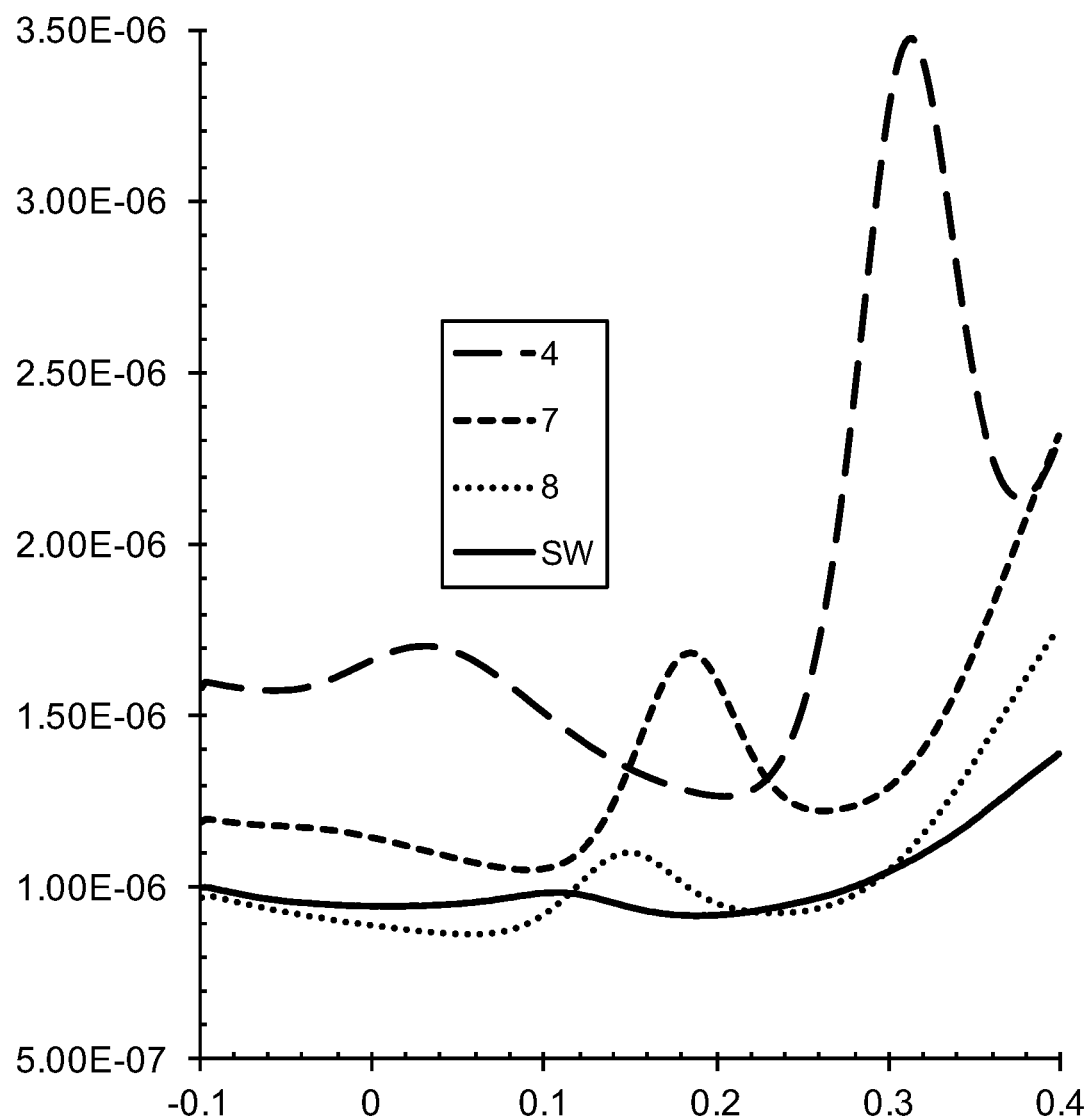
FIG. 2 shows voltammetric response of an electrode comprising a phenol derivative containing a sulphur moiety in accordance with embodiments of the present disclosure, when placed in pH 4, 7 and 8 solutions.

FIG. 2 details the voltammetric response of the modified electrode when placed in pH 4, 7 and 8 solutions. It can be clearly seen that as pH of the species, in accordance with embodiments of the present disclosure, increases the redox wave attributed to the newly formed polymer shifts to negative potentials as the species is easier to oxidise. A plot of peak potential as a function of pH was found to be linear with a sensitivity of 53 mV/pH unit (FIG. 2b).

Figure 3:
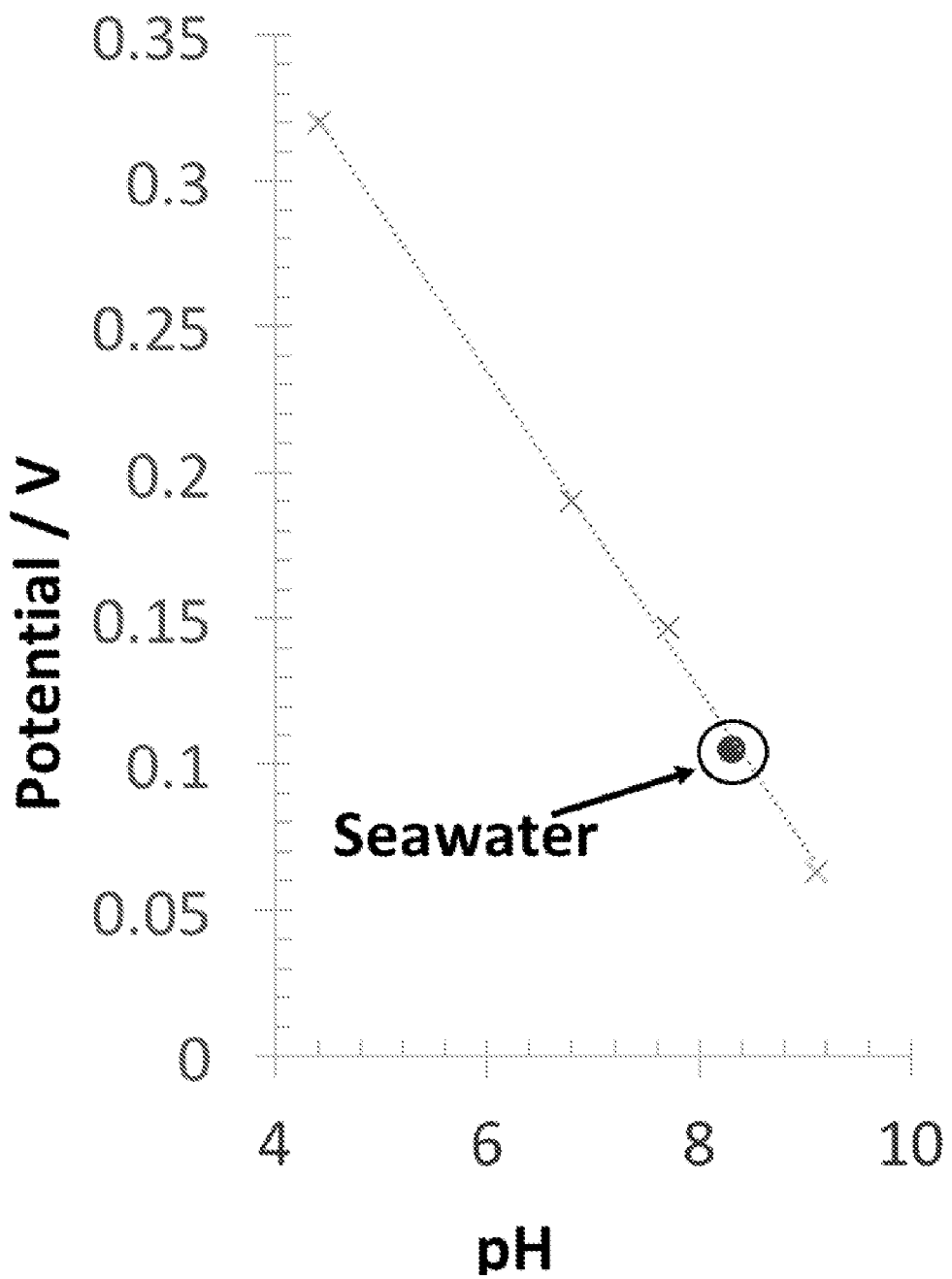
FIG. 3 shows a linear response of an electrode comprising a phenol derivative containing a sulphur moiety, in accordance with embodiments of the present disclosure, to the different pH solutions.

Finally the response of the modified electrode in accordance with some embodiments of the present disclosure was tested in synthetic sea water. The voltammetric profile is overlaid in FIG. 2, which shows the oxidation wave of the polymer moiety at lower potentials than that of the pH 8 solution consistent with the pH being greater than pH 8. Using the data obtained from the calibration plot shown in FIG. 3, the pH of seawater was found to be 8.32, which was found to be consistent with measurements made using a standard glass electrode.

In some embodiments, a redox active species, as disclosed herein, which is sensitive to the analyte concentration/pH, may be used jointly with a redox active compound which is substantially insensitive to the concentration of analyte/pH. This insensitive species, which is independent of analyte concentration, may then function as a reference and the potential of the sensitive compound may be determined relative to the potential of the compound which is insensitive to the concentration of analyte/pH. Possible reference molecules, insensitive to hydrogen ion concentration may comprise molecules containing ferrocene, such as potassium t-butylferrocene sulfonate. In other embodiments, the redox active species may be used with a regular reference electrode, such as a silver/silver chloride reference electrode or the like.

Figure 4:
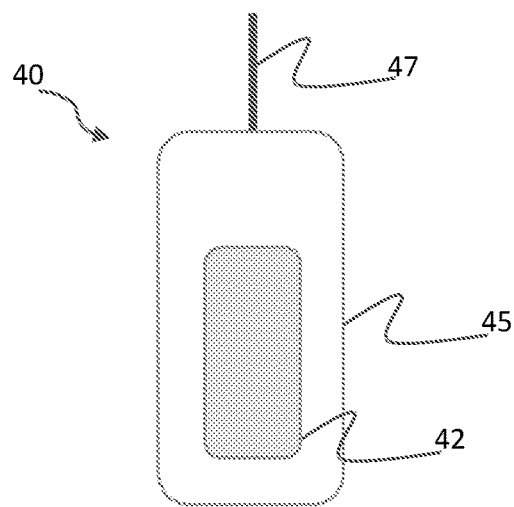
FIG. 4 shows an electrode comprising a phenol derivative containing a sulphur moiety in accordance with embodiments of the present disclosure.

FIG. 4 illustrates an electrode comprising a phenol group includes a sulphur moiety. The electrode 40 comprises a conductive substrate 45 coupled with a redox active species 42 comprising the phenol group includes a sulphur moiety disposed thereon. The electrode 40 further comprises an electrical connector 47 to provide for electronic communication of the electrode. The redox active species, as disclosed here, may be formed on part of the area of the conductive substrate 45. In some embodiments, a reference redox active compound which is substantially insensitive to the concentration of analyte/pH (not shown) may be immobilized on another part of the same substrate to form an electrode with both redox systems or it may be immobilized on another electrode. A reference redox active compound may comprise a ferrocene or the like. The two electrodes may then be connected together so that only a single voltammetric sweep is required. In other embodiments, a regular reference electrode, as is well known in the art, such as a silver chloride electrode or the like or other stable reference may be used as a reference for the electrochemical sensor.

In some embodiments, an ion selective layer (not shown) may be deposited over the redox active species 42. The ion selective layer may act to protect/stabilize the redox active species 42 and/or limit the interaction of the redox active species 42 with only ions that can pass through the ion selective layer.

The redox active species 42 may comprise a phenolic compound having one of the following structures:

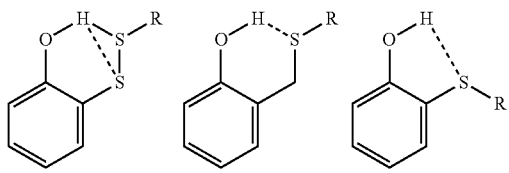

where the substituent R functional group may comprise: alkyl or acyl or aryl (aromatic) or alkyl or alkenyl or alkynl or allyl or nitrile, bonded to S; or alkyl or acyl or aryl (aromatic) or alkyl or alkenyl or alkynl or allyl or nitrile bonded to a hetero atom (where hetero atoms would be one of O, N, P, S) bonded to S, or any other combination thereof.

The electrode may comprise a conducting/conductive substrate, which substrate may comprise: graphene, carbon nanotubes, carbon, glassy carbon, graphite, diamond, boron doped diamond or the like. The conducting/conductive substrate may comprise a wire, such as a carbon or graphene wire. In some embodiments, a paste/mixture of the redox active species 42 may be formed and coupled with the electrode 40. For example a paste/mixture of the redox active species 42 formed with carbon may be disposed in a cavity in the electrode 42. The paste/mixture may include a binder/epoxy to hold the mixture together. In some embodiments the electrode maybe produced by printing conductive inks containing the said redox active pH sensing material onto a substrate using screen printed, pad printed, flexiographic or rotar gravure printed technologies. Graphene and/or carbon nanotubes have been found as good material for the electrode substrate as they are strong, provide good/ regular conductivity, provide for uniform polymerization of the redox active species onto the substrate and can be used in micro-type electrode systems.

Figure 5:
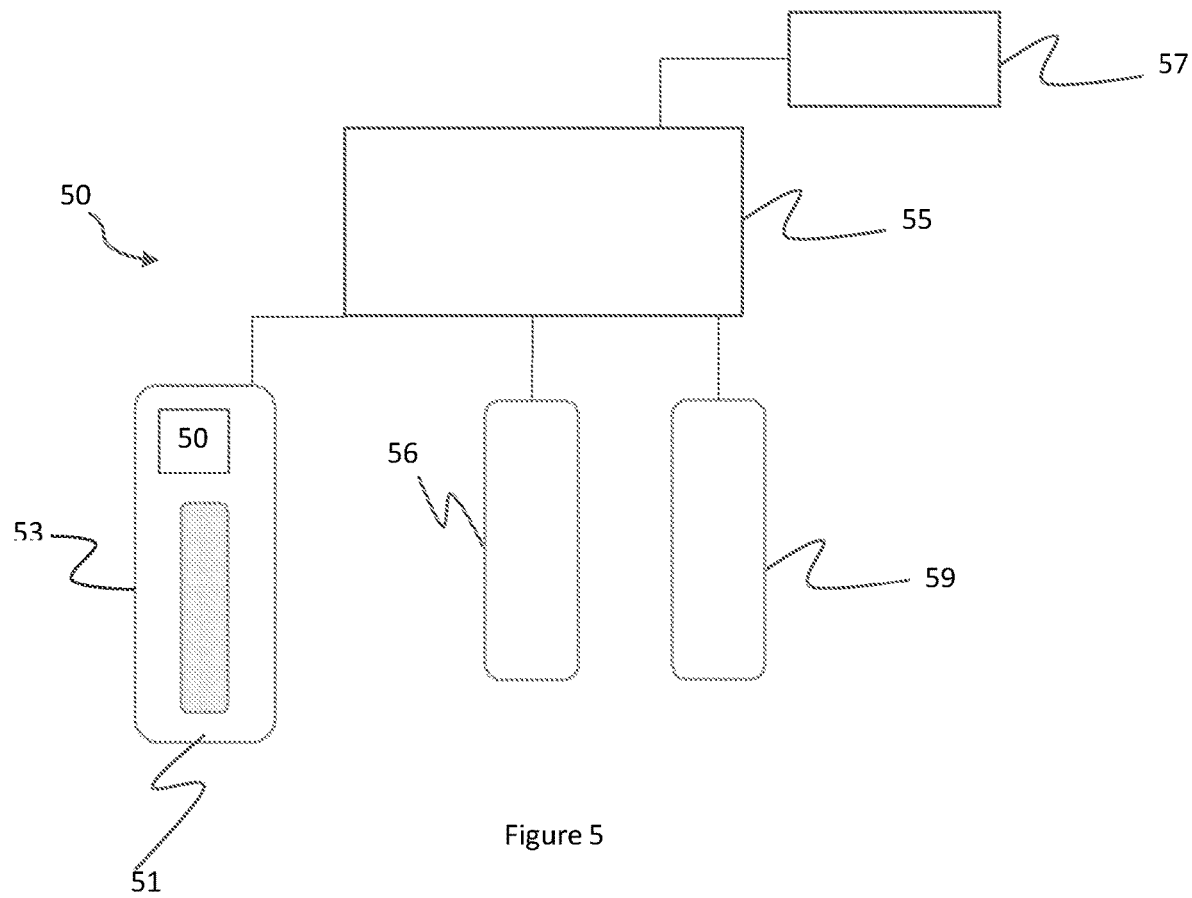
FIG. 5 illustrates a pH sensor comprising the electrode comprising a phenol derivative containing a sulphur moiety in accordance with embodiments of the present disclosure.

FIG. 5 diagrammatically illustrates component parts of a pH sensor 50, which may be used to measure pH, in accordance with some embodiments of the present disclosure. The pH sensor 50 comprises a working electrode 53 comprising a conductive substrate material 52 with a redox active area 51 comprising a phenol group including a sulphur moiety disposed thereon. The redox active area 51 may be deposited on the conductive substrate material 52, polymerized on the conductive substrate material 52, chemically coupled with the conductive substrate material 52, combined with an epoxy and a conductive substance and coupled with the conductive substrate material 52 and/or the like.

The pH sensor 50 comprises a reference electrode 56. The reference electrode may in some embodiments comprise a conductive material with ferrocene immobilized on its surface to serve as a voltage reference. In other embodiments, the reference electrode may comprise any type of reference electrode, such as a calomel electrode, as are well known in the art.

The pH sensor 50 further comprises a counter electrode at 59. The pH sensor 50 comprises a control unit 55, such as a potentiostat or other control unit, which provides electric power and can make measurements. In some embodiments, the control unit 55 may comprise a potentiostat connected to processing circuitry 57 that may control the potentiostat and process data obtained by the potentiostat.

The various electrodes are immersed in or otherwise exposed to a fluid whose pH is to be measured. The control unit 55 may comprise both a sensor and a control unit providing both electrical power and measurement. The control unit 55 may comprise apparatus such as a power supply, voltage supply, or potentiostat for applying an electrical potential to the working electrode 53 and also a detector, such as a voltmeter, a potentiometer, ammeter, resistometer or a circuit for measuring voltage and/or current and converting to a digital output, for measuring a potential between the working electrode 53 and the counter electrode 59 and/or the reference electrode 56 and for measuring a current flowing between the working electrode 53 and the counter electrode 59 (where the current flow will change as a result of the oxidation/reduction of the active redox species).

In some embodiments of the present disclosure, the control unit 55 may sweep a voltage difference across the electrodes and carry out voltammetry so that, for example, linear sweep voltammetry, cyclic voltammetry, or square wave voltammetry may be used to obtain measurements of the analyte using the electrochemical sensor. The control unit 62 may include signal processing electronics to determine peak voltage or the like.

The control unit 55 may be connected to the processing circuitry 57, which is configured to receive current and/or voltage data. This data may be the raw data of applied voltage and the current flowing at that voltage, or may be processed data which is the voltage at peak current. The control unit 55 may be controlled by the processing circuitry 55 giving a command to start a voltage sweep and/or parameters of the sweep such as its range of applied voltage and the rate of change of applied voltage.

Figure 6:
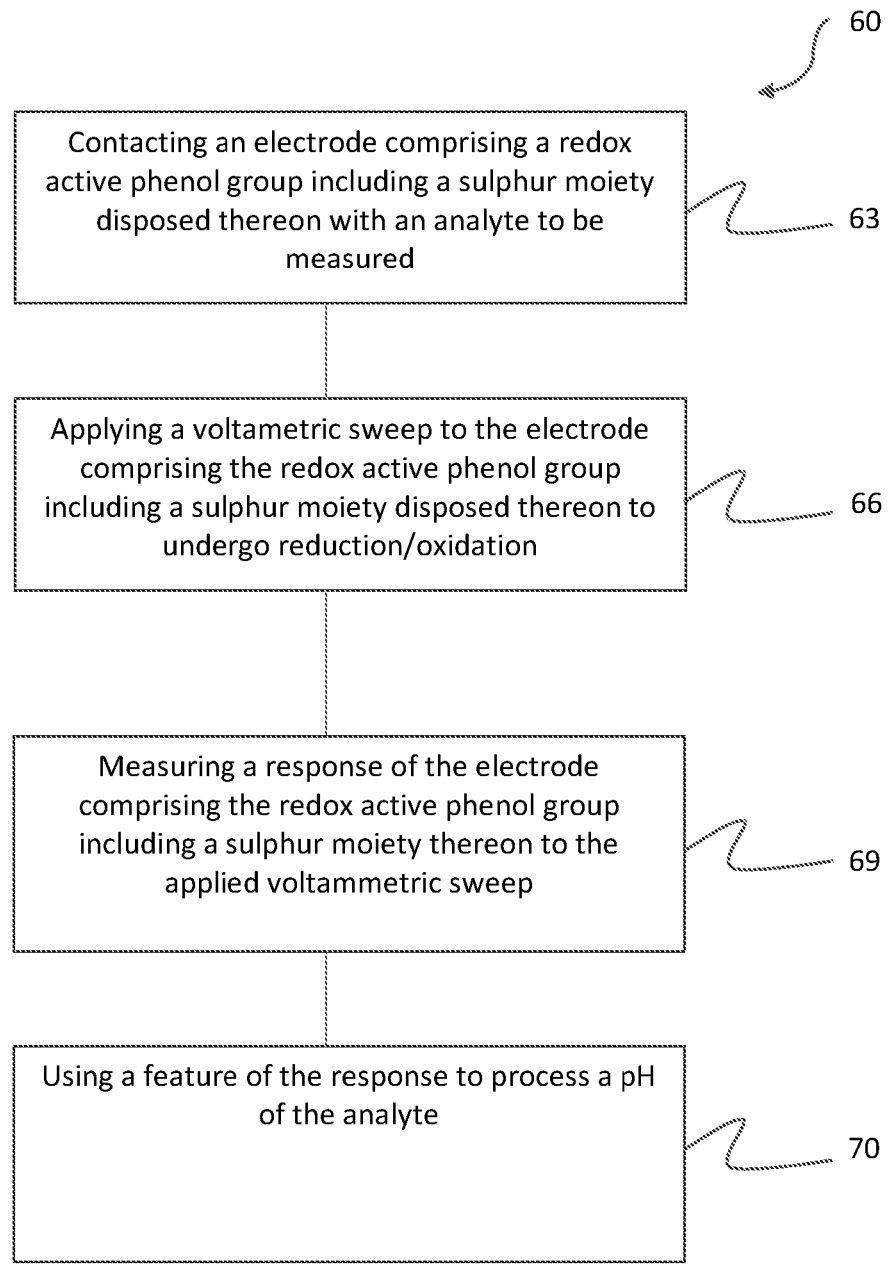
FIG. 6 is a flow-type illustration of a method of measuring pH of a low buffer/low ionic strength solution using a sensor incorporating an electrode comprising a phenol derivative containing a sulphur moiety in accordance with embodiments of the present disclosure.

FIG. 6 is a flow type illustration of a method of measuring pH of a low buffer/ionic strength analyte, in accordance with an embodiment of the present disclosure a phenol group including a sulphur moiety disposed thereon with an analyte to be measured. The analyte comprises a low buffer/low ionic strength analyte such as water, seawater, a saline solution and/or the like.

In some embodiments of the present disclosure, phenol group including a sulphur moiety disposed thereon may comprise derivatives that are based on the formation of hydrogen bonding through either a five (5) member and/or six (6) member ring containing a sulphur-hydrogen bonding where the chemistry forms a polymer on the electrode of the pH sensor that facilitates proton transfer between the analyte being tested and the electrode without passivating the electrode. Some embodiments of the present disclosure provide a pH sensor capable of measuring pH of drinking water, source water, salt water (seawater), saline and/or other low buffer/ionic strength liquids. As such, a sensor in accordance with embodiments of the present disclosure may be used for measuring pH of seawater for ocean monitoring research, measuring pH of water for water management, environmental purposes, measuring pH of low buffer analytes in the food and drink industry, measuring pH of low buffer analytes for medical purposes or in the pharmaceutical industry etc.

In some embodiments of the present disclosure, in step 66, a potentiostat or the like may provide a voltametric sweep to the electrode comprising the redox active phenol group including a sulphur moiety disposed thereon to undergo reduction/oxidation.

In step 69 a response of the electrode comprising the redox active phenol group including a sulphur moiety disposed thereon to the applied voltammetric sweep is measured. The response of the electrode is dependant upon the concentration of hydrogen ions in the low buffer analyte interacting with the active redox species.

In step 70 a feature of the response is processed to determine a pH of the low buffer analyte. In some embodiments, the feature may be a potential of a peak in the response. In other embodiments it may be a location of maximum change or a turning point in the response or the like.

While the principles of the disclosure have been described above in connection with specific apparatuses and methods, it is to be clearly understood that this description is made only by way of example and not as limitation on the scope of the invention.

The invention claimed is:

1. An electrochemical sensor for measuring pH of water or seawater, comprising:
a working electrode comprising a phenolic compound, wherein the phenolic compound includes a sulphurous atom attached either directly or indirectly to an aromatic ring of the phenolic compound and configured to form a hydrogen bond with a hydrogen atom associated with a hydroxyl moiety of the phenolic compound, wherein the phenolic compound comprises one of:

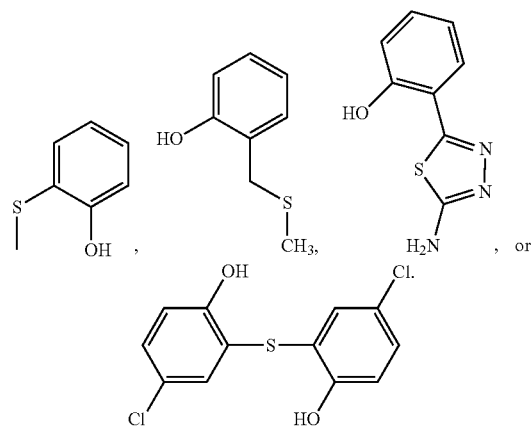

2. The electrochemical sensor of claim 1, wherein the phenolic compound is polymerized through electrochemical oxidation to form a redox active polymer, and wherein the formed redox active polymer does not passivate the working electrode.

3. The electrochemical sensor of claim 1, wherein the phenolic compound has one of the following structures:

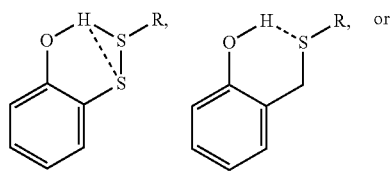

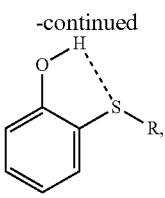

where R comprises: an alkyl or acyl or aryl (aromatic) or alkyl or alkenyl or alkynl or allyl or nitrile, bonded to S; or an alkyl or acyl or aryl (aromatic) or alkyl or alkenyl or alkynl or allyl or nitrile bonded to a hetero atom bonded to S, wherein the hetero atom comprises O, N, P, S, or any combination thereof.

4. The electrochemical sensor of claim 1, wherein the working electrode comprises: the phenolic compound solvent cast on a conducting substrate, the phenolic compound included in a carbon paste or a carbon epoxy, the phenolic compound pressed into or onto a conducting substrate, the phenolic compound pressed into a cavity in a conducting substrate, the phenolic compound polymerized onto a conducting substrate, the phenolic compound immobilized on a carbon electrode, or the phenolic compound screen-printed onto a conducting substrate.

5. The electrochemical sensor according to claim 4, wherein the conducting substrate or the carbon electrode comprises graphene or carbon nanotubes.

6. The electrochemical sensor according to claim 4, wherein the conducting substrate or the carbon electrode comprises a graphene or carbon wire.

7. The electrochemical sensor according to claim 4, wherein the carbon paste or carbon epoxy comprises graphene or carbon nanotubes.

8. The electrochemical sensor according to claim 4, wherein the working electrode comprises at least one of glassy carbon, graphite diamond, carbon nanotubes, or graphene.

9. The electrochemical sensor according claim 1, wherein the working electrode comprises an ion selective layer.

10. The electrochemical sensor according to claim 1, wherein the electrochemical sensor comprises a further redox species as a reference.

11. The electrochemical sensor according to claim 1, wherein the water comprises a saline solution.

12. The electrochemical sensor according to claim 1, wherein the phenolic compound is insoluble.

13. A method for manufacturing the working electrode of claim 1, comprising polymerizing the phenolic compound onto a conducting substrate.

14. A method for measuring pH of water or seawater, the method comprising:
contacting a working electrode of an electrochemical pH sensor with water or seawater, wherein the working electrode comprises a phenolic compound and the phenolic compound includes a sulphurous atom attached either directly or indirectly to an aromatic ring of the phenolic compound and is configured to form a hydrogen bond with a hydrogen atom associated with a hydroxyl moiety of the phenolic compound, wherein the phenolic compound comprises one of:

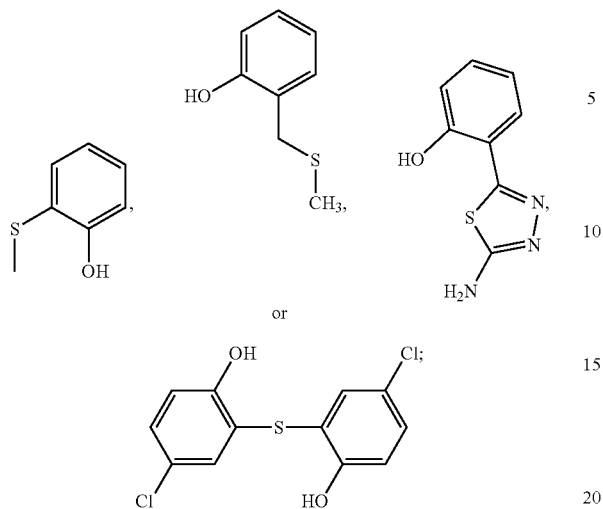
applying a voltammetric sweep to the working electrode; and
determining the pH of the water or seawater from a voltammetric response of the working electrode.
* * * * *